(12) United States Patent
Hämäläinen et al.

(10) Patent No.: US 10,580,532 B2
(45) Date of Patent: Mar. 3, 2020

(54) METHOD AND AN APPARATUS FOR DETERMINING TRAINING STATUS

(71) Applicant: Firstbeat Technologies Oy, Jyväskylä (FI)

(72) Inventors: Kaisa Hämäläinen, Jyväskylä (FI); Aki Pulkkinen, Jyväskylä (FI); Mikko Seppänen, Jyväskylä (FI); Tuomas Järvinen, Jyväskylä (FI); Joonas Korhonen, Jyväskylä (FI); Tero Myllymäki, Jyväskylä (FI)

(73) Assignee: Firstbeat Technologies Oy, Jyväskylä (FI)

( * ) Notice: Subject to any disclaimer, the term of this patent is extended or adjusted under 35 U.S.C. 154(b) by 251 days.

(21) Appl. No.: 15/850,642

(22) Filed: Dec. 21, 2017

(65) Prior Publication Data

US 2018/0174685 A1 Jun. 21, 2018

Related U.S. Application Data

(60) Provisional application No. 62/437,453, filed on Dec. 21, 2016.

(51) Int. Cl.
| | |
|---|---|
| A61B 5/0205 | (2006.01) |
| G16H 50/30 | (2018.01) |
| A61B 5/083 | (2006.01) |
| A61B 5/024 | (2006.01) |
| G16H 20/30 | (2018.01) |
| A63B 24/00 | (2006.01) |

(52) U.S. Cl.
CPC ........... *G16H 50/30* (2018.01); *A61B 5/0205* (2013.01); *A61B 5/02405* (2013.01); *A61B 5/02438* (2013.01); *A61B 5/0833* (2013.01); *G16H 20/30* (2018.01); *A63B 2024/0065* (2013.01)

(58) Field of Classification Search
CPC ........... A61B 5/02405; A61B 5/02438; A61B 2503/10; A61B 2562/0219; A61B 5/0205; A61B 5/0833; A61B 5/1112; A61B 5/1118; A61B 5/1128; A61B 5/4815; A61B 5/486; A61B 5/4884; A61B 5/681; A61B 5/6898; A61B 5/741; A61B 5/743; G16H 20/30; G16H 40/63; G16H 40/67; G16H 50/30; A63B 2024/0065
See application file for complete search history.

(56) References Cited

U.S. PATENT DOCUMENTS

| | | | |
|---|---|---|---|
| 7,192,401 | B2 | 3/2007 | Saalasti et al. |
| 7,330,752 | B2 | 2/2008 | Kettunen et al. |
| 9,519,755 | B2 | 12/2016 | Saalasti et al. |
| 2014/0088444 | A1 | 3/2014 | Saalasti et al. |
| 2015/0269825 | A1* | 9/2015 | Tran ................ G08B 21/0446 340/539.12 |
| 2016/0324462 | A1 | 11/2016 | Hamalainen et al. |

* cited by examiner

*Primary Examiner* — George Manuel
(74) *Attorney, Agent, or Firm* — Maier & Maier, PLLC

(57) ABSTRACT

A method and apparatus for determining training status from a group of alternatives from a plurality of exercises, where a user has frequently monitored exercises with at least heart rate being measured by a host process, which outputs selected variables for calculating the training status by a child process.

13 Claims, 11 Drawing Sheets

| Training Status | Description | Load | Fitness | Training load decreasing? | Training that may lead to a state | Recommended actions |
|---|---|---|---|---|---|---|
| Detraining | Your training has been too easy and your fitness level is therefore decreasing. Increase your activity level! | Low | Decreases | | At least 7 day period of easy training causing decreasing fitness level OR no training at all during last 7 days. | Do something – anything! |
| Recovery | Your body has recovered from previous training. You are ready to start training harder again! | Low to moderate | Steady | YES | User is having an easier training week after 2-3 harder training weeks. Training load may be low but "tapering" does not cause increase in performance. | You are ready for hard workouts! Detraining will start in a couple of weeks if training load is kept low. |
| Maintaining | You have been training enough to maintain your fitness level. If willing to improve try to break the pattern! | Low to moderate | Steady | | Training load is similar to user's long term training history. Typical training does not disturb body's homeostasis sufficiently to cause fitness increases. | This type of training seems to be enough to maintain your fitness level. If willing to improve try to break the pattern! You could try to add more variation into your training; hard intervals balanced by easy recovery workouts |
| Productive | Good work! Your recent training has really built up your fitness level! Add load progressively to maintain stimulus but remember to plan recovery periods as well. | Moderate to High | Steady or increases | | Training load is moderate to high. Body is able to recover well from training and fitness starts to increase. | Keep up the good work! Add load progressively to maintain stimulus. Remember to plan recovery periods as well. |
| Peaking | Easy training after harder period has really peaked your fitness level. Still remember that Detraining will start in a couple of weeks if training load is kept low. | Decreases from high to low | Increases | YES | Training load has been high recently. After a few days or a week of significantly decreased training fatigue is starting to disappear and fitness level increases starts to show up. | Race anyday! Detraining will start in a couple of weeks if training load is kept low. |
| Overreaching | You have now crossed the limit of sustainable training load and your fitness level is decreasing. Start easier training period soon and we may see you even Peaking after that! | High | Decreases | | A period of one week or longer of high training load during which body is not able to fully recover between exercises. This leads to overreaching state where fitness level starts to decrease. | Focus on recovery and easy recovery training. |
| Unproductive | Your training seems to be OK but your fitness level decreases. Unless you are sick or getting sick, you need to consider other things where you can improve your recovery: e.g. by sleeping better or by | Moderate | Decreases | | Training seems good relative to user's history and fitness level but still fitness level decreases. This may be caused by illness, poor sleep, work-related stress, or other things that impair person's | Your training seems to be OK but your fitness level decreases. Accordingly, unless you are sick, you need to consider other things where you can improve your recovery: e.g. better |

Fig. 5

METHOD AND AN APPARATUS FOR DETERMINING TRAINING STATUS

FIELD

The present method and apparatus relate to determining training status from a group of alternatives during from a plurality of exercises, where a user has frequently monitored exercises with at least heart rate being measured by a host process, which outputs selected variables for calculating the training status by a child process.

BACKGROUND

It is possible for everyone to improve their cardiorespiratory fitness through effective planning of activities. Exercise sessions must be performed frequently enough, and the sessions should regularly include both easier exercise sessions as well as more demanding sessions. In general, sessions should have variation both in their intensity and their duration, and this creates a "training load", a measure of how much physical work has been performed through activity. In addition to changes in daily training load, weekly and seasonal training must include variation. The variation in training load is needed to continue fitness development while avoiding injuries or developing overtraining symptoms.

Monitoring training load and fitness level development is important to ensure athletes train at an optimal level towards their goal and avoid overloading. Appropriate load and fitness monitoring aids in determining whether an athlete is adapting to a training program and is minimizing the risk of overtraining, developing illness, and/or injury.

To be able to make decisions on future training a user needs to know the current trajectory of their training, referred to as their training status. At certain points in a user's training, they may wish to decrease or increase training in specific ways to elicit a specific reaction, such as peaking for an important race. This requires not only information on each individual exercise, but information on a plurality of exercises to determine the cumulative effect they have had on a user's fitness.

Training status using data from multiple exercises is not something that is currently available. At first sight that kind of application seems to need a lot of resources. Embedded systems, such as heart rate monitors, fitness devices, mobile phones, PDA devices, tablet computers, or wrist top computers have quite limited CPU and memory resources to be used by any utility application. Those resources are only a fraction of that of an ordinary PC. This is a challenge for an implementation of any physiological method.

SUMMARY

The current invention is directed towards a method and apparatus to determine training status from a group of discrete alternatives from a plurality of exercises, where the method can be implemented in an embedded device having limited CPU and memory resources and having a host system. In one embodiment the host system uses ETE and THA-libraries, where the ETE is a real-time heart rate analysis library, and THA is a training history analysis library. THA-software is called and executed temporarily to calculate training status value.

In a preferable embodiment the selection of key variables minimizes the demand of resources, particularly RAM memory, and more specifically dynamic memory. The demand of resident memory is very limited, when only characteristics of each exercise are stored.

Training status calculation uses training history data including all kinds of exercise type data. The calculation analyzes absolute training load and saves it to internal memory. If the type of exercise is walking, running or cycling, the user's fitness level is also analyzed and stored with training load information. Preferably, there is 14 days training history available, and a minimum 7 days. The system will typically store and take into consideration up to 50 days training history It can be seen from the literature on physical training that the harder the training has been, the more the homeostasis of the body is disturbed. The more that the homeostasis can be disturbed, the greater the adaptations that can be created in the body and the improvements in physical condition that derive from the adaptations. Thus, wherein the variable of the training load may be a peak value regarding training effect measured as disturbance level of homeostasis.

Training status is determined based on three main parameters: changes in fitness level (represented by VO2max) or a specific HRV-variable, current short-term training load, and change in short-term training load with respect to previous training. Training status calculation analyzes previous training data; current training load, training load changes and variation in fitness level.

We are using following terms regarding:
Short-term=7 days or less
Long-term=More than 7 days
These are exemplary definitions.

In optimal situations, training status is analyzed with fitness level results. In this situation short-term and long-term training load can be compared to fitness level development. If VO2max is not determined frequently enough to monitor VO2max development (for example, no VO2max during the previous 2 weeks), training status is determined based on training load history data with respect to personal background parameters. Below is first described training status analysis when the VO2max information is available. Later on there are exemplary embodiments considering training status determination without fitness level information. The parameter VO2max (fitness level) or HRV-variable relates to the user's ability to execute training.

In one exemplary embodiment, a method for determining training status as an alternative of a fixed group of alternatives each of them depicting a unique physical condition of the user, wherein each exercise is monitored using the heart rate sensor, whereby heart rate data is stored in a memory during the exercise, and
  chosen exercise characteristics of each executed exercise are determined using stored heart rate data in the memory, and
  after each exercise the determined characteristics of each executed exercise are stored in a memory, the chosen exercise characteristics including values of at least following variables:
  a date of the exercise,
  a value depicting physical readiness during the exercise
  a value depicting a training load of the exercise
and when the plurality of exercises has been executed, values of selection variables are calculated using the stored exercise characteristics in the memory, and the training status is determining using sequential pre-determined selection rules, each rule connected to one unique variable of said selection variables, where the each selection rule using a calculated value of its selection variable limits the number of remaining alternatives and after all selection rules has been sequentially used, only one alternative is selected.

The first variable may present a VO2max trend of the user, the second variable may present a weekly training load (WTL) and the third variable a WTL trend.

The parameter "physical readiness" may refer to the body's capability to perform sustained physical work, particularly related to exercisers or athletes, based on previous training history and may also refer to a fitness level (VO2Max), heart rate variability measurements (FIG. 10).

The parameter "physical readiness" typically refers to a user's fitness level (VO2max), but may also refer to measured heart rate variability (HRV, FIG. 10), and how describes how a user has recovered from physical exercise and how capable their body is to perform more exercise.

The first selection may select a group from a set of groups covering all said alternatives and the second selection may select the training status alternative or a pair of alternatives from the first selected group.

It may be understood that the first, second and third variables may be in a different order. However, the chosen selection of variables is an important factor to achieve accurate results with a minimal use of CPU/memory resources.

In one embodiment the characteristics of exercises are calculated by a host process having a specific library software (ETE) and a resident memory to store the characteristics for later use. Then a software forming a child process to calculate an actual training status is provided by separate library software (THA), where the child process uses minimum amount of dynamic memory and vanishes after it has entered the result to the host process.

On the other hand, it is possible to implement said three selection rules as a 3-dimensional look-up table, where the result is picked by a vector having values of said three parameters.

According to another embodiment there is a third variable to be classified and obtaining a third selection for selecting the training status from said pair of alternatives, and wherein the third variable may be a training load trend.

The actual fitness trend may be determined by daily monitored VO2max, particularly a calculation window with a plurality of days may be used. A weighted fitting on a line may be used so that the newer results are emphasized more.

In one embodiment, the number of training status alternatives is at least 5, these alternatives comprising at least "Detraining", "Maintaining", "Recovery", "Overreaching" and "Productive".

Relative weekly training load may be determined according to VO2max and/or training history based activity class and absolute weekly training load (a sum of a plurality of days). In another embodiment there can be two additional statuses: "Recovery" and "Peaking" in use-cases where longer exercise history can be inputted to calculation.

In another embodiment values of selected variables of each day are recorded in a sliding window of a plurality of past days, the selected variables including at least the highest VO2max, its type of exercise, a sum of peaks of training loads, the fitness trend being calculated from the values of the highest VO2max of a same type. The memory demand and calculation time can be minimized with this selection of variables. The trend may be calculated using VO2max values of same type exercise (running, cycling). The types of variables are selected as small as possible and a minimum amount of data is recorded. The calculation may be run quite seldom, usually only when a new exercise exists. A calculation takes only a couple of milliseconds.

The method could be implemented in any device comprising a processor, memory and software stored therein and a user interface, for example, a heart rate monitor, fitness device, mobile phone, PDA device, wrist top computer, and the like. The implementation may use a minimum amount of RAM memory and CPU-time.

BRIEF DESCRIPTION OF THE FIGURES

Advantages of embodiments of the present disclosure will be apparent from the following detailed description of the exemplary embodiments. The following detailed description should be considered in conjunction with the accompanying figures in which the figures may show exemplary embodiments of the method and apparatus for determining training status from a group of alternatives during exercise season. Figures are only exemplary and they cannot be regarded as limiting the scope of invention.

FIG. 5 represents a training status description table

Figure 1A:
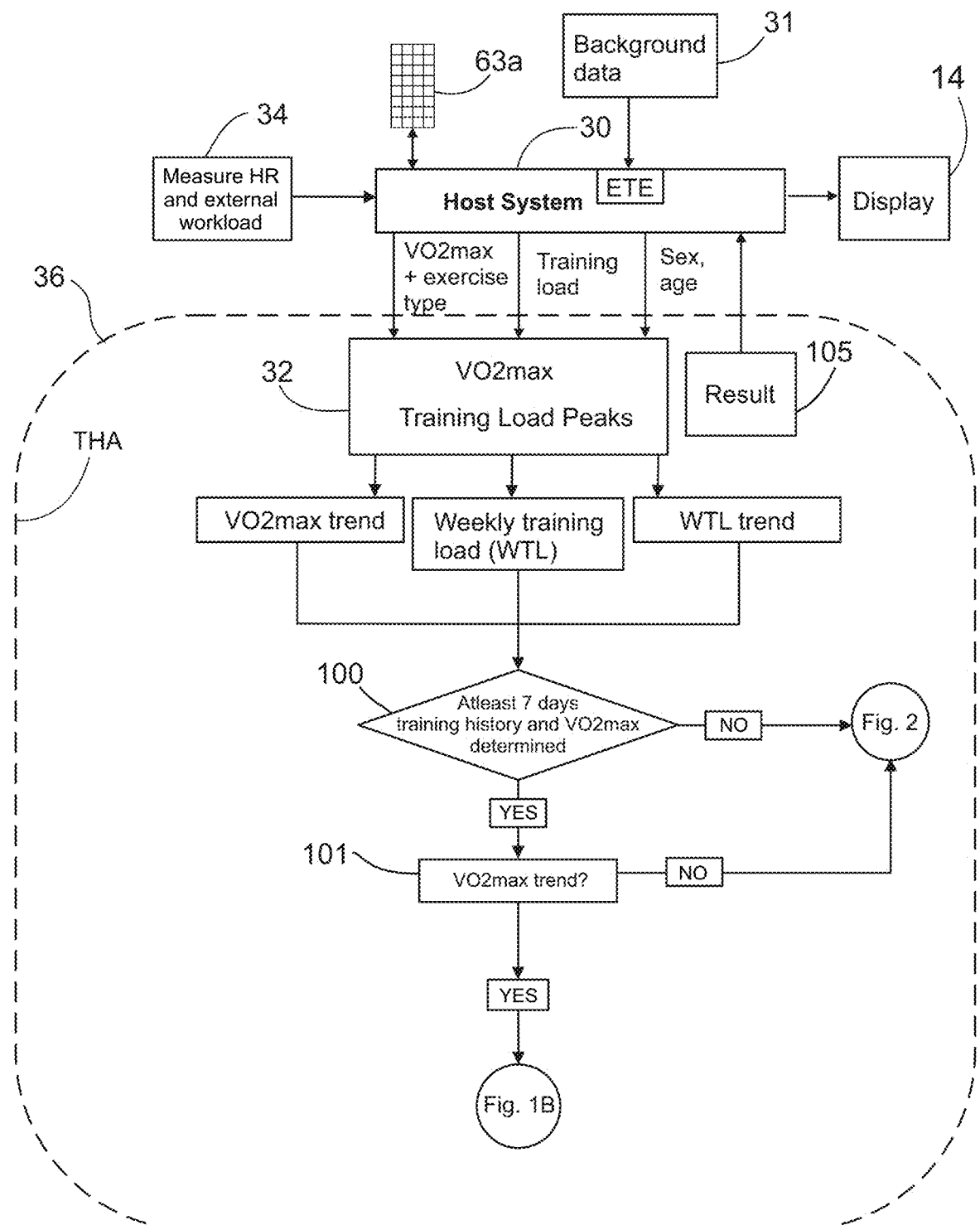
FIGS. 1A and 1B are a two-part schematic that represent the steps of training status calculation steps of a child process and its connection to a host system

| Term or abbreviation | Definition |
| --- | --- |
| HR | Heart rate (beats/min) |
| HRmax | Maximum heart rate (of a person) (beats/min) |
| VO2 | Oxygen consumption (ml/kg/min) |
| Readiness | Fitness level or HRV-value depicting user's ability to exercise |
| VO2max | Fitness level, maximum oxygen consumption capacity of a person (ml/kg/min) |

| Term or abbreviation | Definition |
|---|---|
| % VO2max | Measured VO2 relative to VO2max of a person |
| Training Load | A measure of the amount of training a person has performed, and may take various forms. One can measure training load in a single session, or cumulatively over a period of time. More or harder training will have a higher training load. |
| Peak value of exercise | Value 1-5 according to a training load sum during a week and user's activity class |
| HRV | Heart rate variability meaning the variation in time interval between successive heart beats. The magnitude of heart rate variability may be calculated from electrocardiographic or photoplethysmographic signals, for example. |
| EPOC | Excess post-exercise oxygen consumption. As it can be nowadays estimated or predicted - based on heart rate or other intensity derivable parameter - it can be used as an cumulative measure of training load in athletic training and physical activity. |
| TRIMP | Training Impulse score. A cumulative measure of the impact of a training session |

DETAILED DESCRIPTION

Aspects of the invention are disclosed in the following description and related drawings directed to specific embodiments of the invention. Alternate embodiments may be used without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", embodiments" or "invention" do not require that all embodiments of the invention include the discussed feature, advantage or mode of operation.

Many fitness applications measure heart rate as well as other external workload dimensions like speed. In a preferred embodiment, the host system 30 determines fitness level as a VO2max value. It may also record previous exercises with information of the data of activity (e.g. running/cycling) and produce information to be used in the training status calculation by a child system 36. The host system 30 outputs the values of selected variables for a child system, where a calculation module 32 calculates values to be substituted in the selection functions. The following variables may be needed regarding each exercise: VO2max and a type of exercise (e g running/cycling), training load data usually directly as a training load peak-value, and sex and age of the user as well as activity class. Default values (excluding sex) may be used when the device determines better values according to one or more exercises. The calculated values are VO2max trend, weekly training load (WTL) and WTL trend.

Figure 1B:
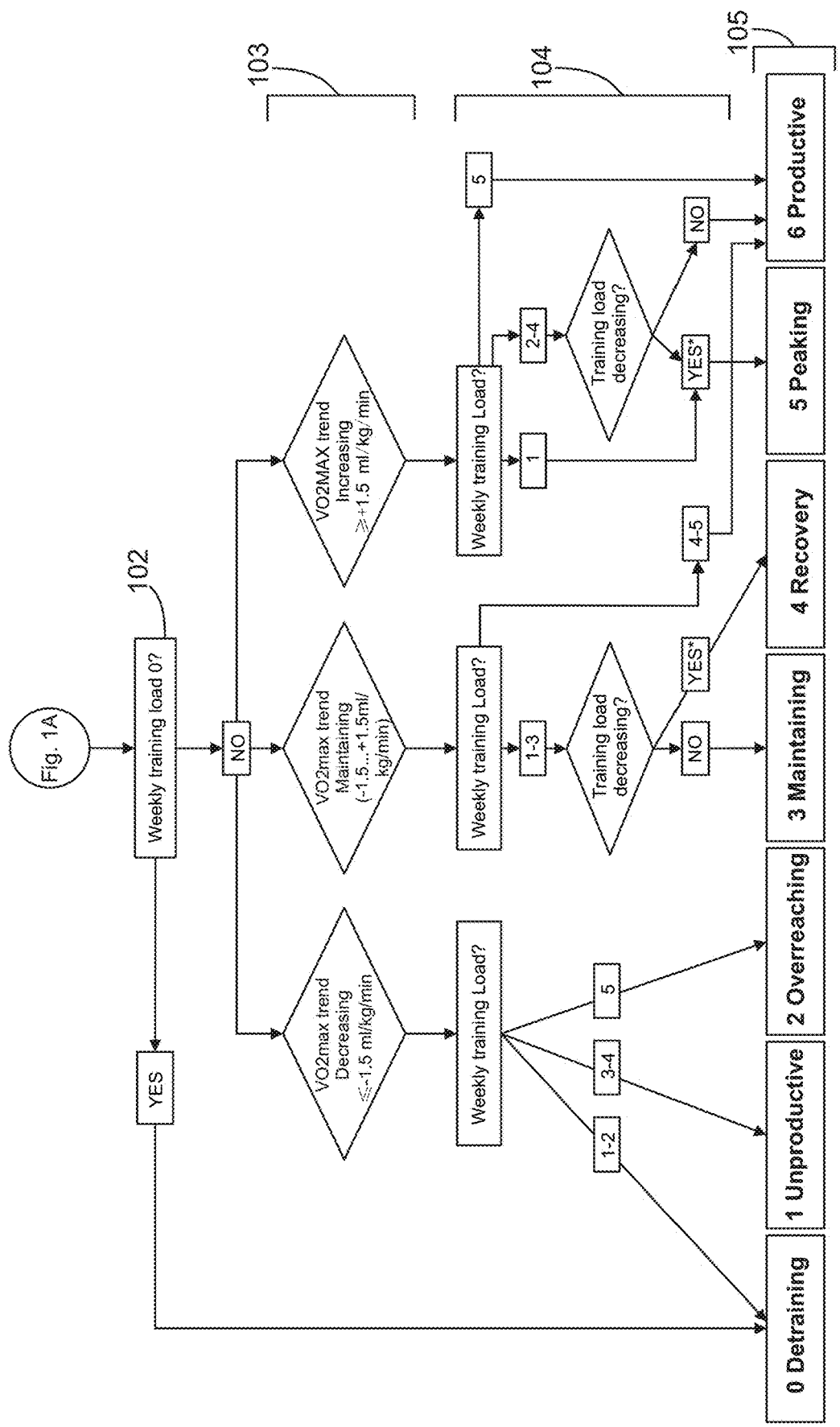

When at least 7 days of training history data is available training status can be determined using the follow steps, as shown in FIG. 1, and will be described in further detail below.
  1. VO2max is calculated in a host system from each exercises' heart rate (e.g. ECG, HRV, PPG) and external workload (e.g. GPS, accelerometer, power output, and the like) data
  2. Absolute training load (EPOC+TRIMP) is calculated in a host system from each exercise heart rate and external workload data
  3. Transferring VO2max and absolute training load to a child system as an input
  4. VO2max trend is calculated
  5. Absolute Weekly Training load is calculated
  6. Relative weekly training load in proportion to VO2max (and/or 28 day training history) is calculated
  7. Training load trend is calculated
  8. The number of consecutive rest days are defined
  9. Determine direction of fitness level development (increasing, decreasing or maintaining)
  10. Processing the information about VO2max trend, relative weekly training load and Training load trend and determine training status as shown in FIG. 1B.

Referring to FIG. 1A, a host system 30 and a child system 36 is shown. The host system receives background data, which may include demographic information of the user like gender, age, height, weight, physiological data like resting or maximum heart rate, or other well-known variables. The host system also receives measured heart rate, external workload data, and may also receive other context data such as information on previous exercise sessions or exercise type information.

The training load is a peak value regarding training effect measured as a disturbance level of homeostasis.

Exercise heart rate may be received from any type of available heart rate data collection apparatus, such as electrocardiogram (ECG) or photoplethysmogram (PPG). In an exemplary embodiment, these collection apparatuses include portable devices such as a wrist top device with a heart-rate transmitter, a mobile device such as a phone, tablet or the like, or other system having CPU, memory and software therein.

External workload may be derived from any suitable form of device that can collect external workload, depending on the activity in question, and may include global positioning satellite data, accelerometers, measured power output, positioning detection using Wi-Fi, motion capture cameras, or other detection devices of a similar nature known to a person of average skill in the art. The VO2max value is calculated according to e.g. a method disclosed in US2014088444 (A1) "METHOD AND SYSTEM FOR DETERMINING THE FITNESS INDEX OF A PERSON" incorporated herein.

Within the host system 30, measured heart rate and external workload data are used to determine fitness level (VO2Max) and training load peak. Training load is defined using existing physiological values that represent the impact a particular exercise session has on the body, often influenced by the intensity and the duration of the exercise session. In an exemplary embodiment, the physiological values of Excess Post-Exercise Oxygen Consumption (EPOC) and Training Impulse (TRIMP) are used, though other known values that serve a similar purpose may also be used. By measuring training load peak of values like EPOC or TRIMP, a singular absolute training load value for each exercise session is calculated and stored. If there are multiple training sessions being held in one day, the absolute training load value for a particular day may also be calculated as a sum of each session's training load peak value.

The host system 30 transfers the calculated VO2Max and absolute training load and background parameters (e.g. age, gender, height and weight) to child system 36 as an input and stores them to a resident memory.

VO2Max and absolute training load are loaded into calculation module 32 of child system 36, which calculates values that will be used in the selection functions including VO2Max trend, relative weekly training load (WTL), and WTL load.

The child system 36 enters result, the chosen training status value back to the Host system 30, which may show it on the display 14. Optional additional information is also submitted to the Host System 30 (not shown).

Figure 2:
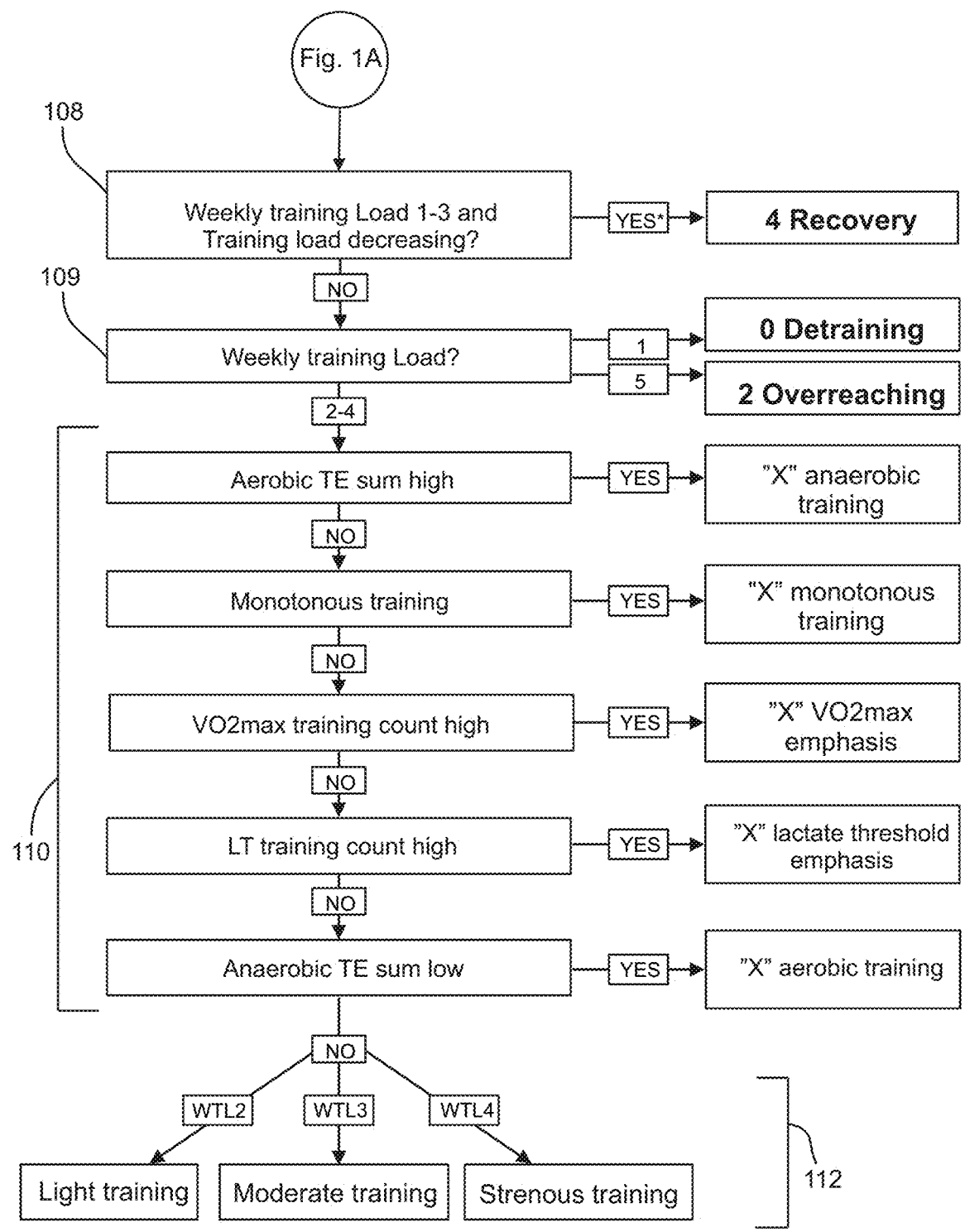
FIG. 2 represents calculation of limited feedback without VO2max trend

The output of data from calculation module 32 begins the steps 100-105 of calculating training status. Step 100 determines if there sufficient training history and fitness level information. In an exemplary embodiment, training history is at least seven days of training history. The seven days of training history need not be the previous seven days or even seven consecutive days, rather, a cumulative seven days of training history over a non-specific length of time. Fitness level is represented by a VO2Max value. A "yes" result for both data allows proceeding to the next step. A "no" result may result in the system calculating an alternative limited training status information as shown in FIG. 2, which will be described in further detail below.

Referring still to FIG. 1A, in step 101 the system calculates whether the information supplied by the host system is sufficient a VO2Max trend. If it is not determined the system does not have the requisite values, fitness level development is not known, then the system may also proceed to the limited training status selection processes shown in FIG. 2

Referring now to FIG. 1B, for any training status greater than "0—Detraining", there must be at least some amount of training load in the previous 7 days. Step 102 determines whether the value of weekly training load being greater than zero. A weekly training load of zero means that the user has not performed any recorded exercise in the past seven days that has measured HR and external workload values recorded by a host system 30.

With the training load being determined as being greater than zero, the system proceeds to step 103 of calculating VO2max trend. Calculation of VO2max trend is performed as follows: calculate in the 14-day window weighted fitting a line so that the newer results are emphasized more. This line's slope k describes VO2max growth per day. VO2max growth with the current trend in month is 28*k. Below is an example VO2max trend (ml/kg/min/month) interpretation:

Decreasing($\leq$−1.5 ml/kg/min/month)
Maintaining(−1.5<+1.5 ml/kg/min/month)
Increasing ($\geq$+1.5 ml/kg/min/month)

In step 105, an output of a training status is produced, summarized by a range of terms. In an exemplary embodiment, the training status discrete alternatives described herein include "0—Detraining", "1—Unproductive", "2—Overreaching", "3—Maintaining", "4—Recovery", "5—Peaking", and "6—Productive". The use of these particular terms is not necessarily required to adequately define the training statuses, and similarly appropriate words may also be used in their place. FIG. 5 shows further elaboration of each training status and text description of the criteria and typical training background resulting in a particular training status—as well as recommended user action for each status. It should be that noted other terms or training statuses not specifically identified here may also be possible as appropriately differentiated terminology and other variables are made available.

Figure 1C:
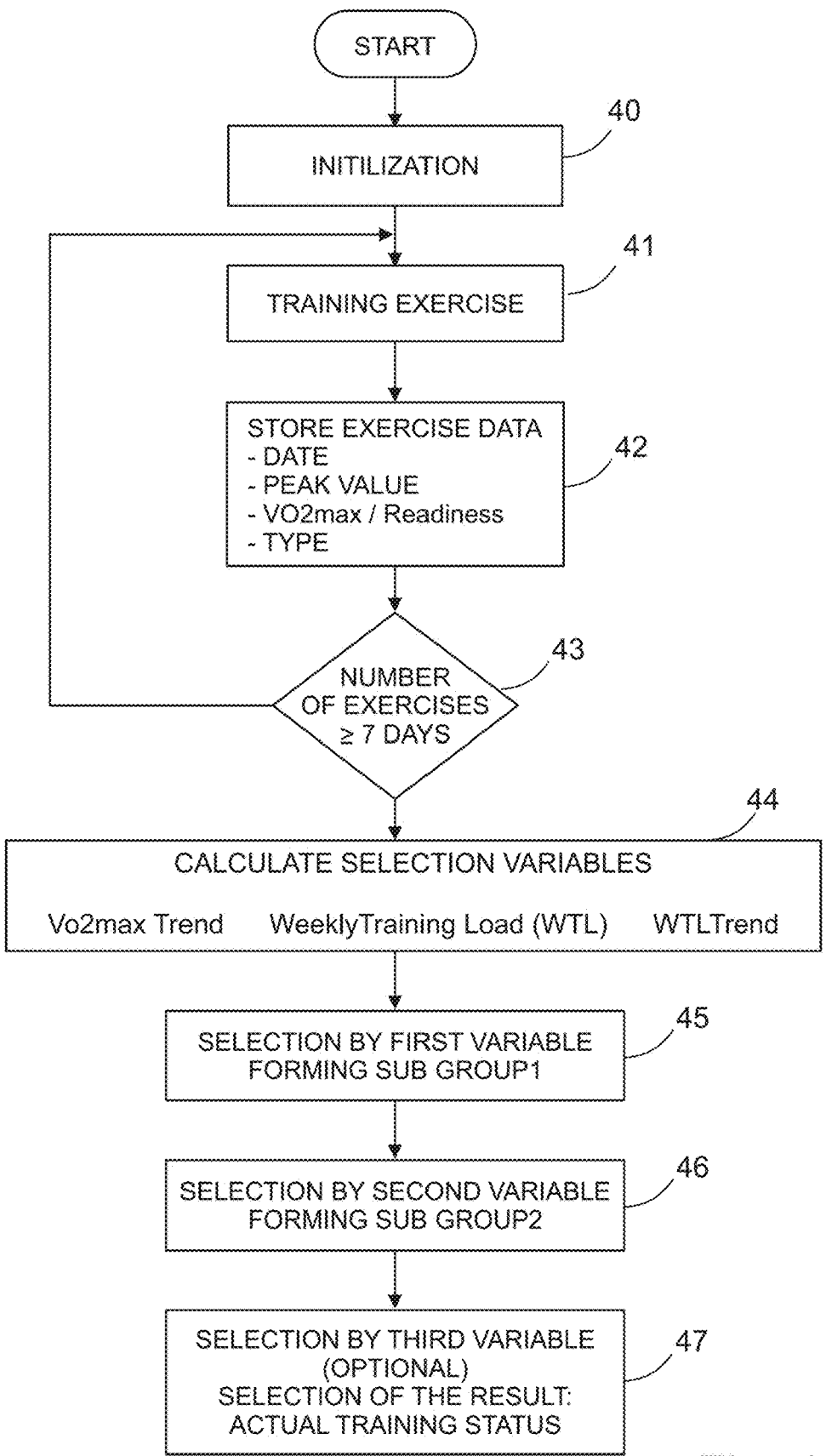
FIG. 1C presents a flowchart visualizing the process of determining the training status

The Flowchart of the Execution of Software (FIG. 1C)

The host process is continuously running by a host system 30. After, a start software initializes (step 40) the child process and populates background data in runtime registers. When an exercise starts the host process call specific software form the library ETE, which take care ordinary calculation of monitoring exercises and calculate desired physiological results, including characteristics of each exercise. Each exercise is monitored in step 41 and after that the characteristics, i.e. the values of specific parameters are stored to a resident memory in step 42. Those specific parameters are date, peak value, VO2max or readiness (based on HRV) and a type of the exercise.

In a step 43 there is a condition whether there are enough data for calculation of training status.

If number of exercises is to low, the execution returns to monitor next exercise, otherwise the child process is called from library THA. The characteristics are fed to runtime registers and the selection variables are calculated in step 44.

In three sequential selection (steps 45, 46, 47) the result is picked up (step 105 in FIG. 1B). The step 45 selects subgroups I using value of VO2maxt trend.

Few results can be picked up directly in certain combinations in next step 46 using the value of the weekly training load, otherwise there are subgroups II each having two or more alternatives. The result will be obtained always at least using third selection in step 47 using value.

Absolute and Relative Training Load and Training Load Trend Calculation

Absolute training load is a calculation of the total training load over a selected period of time, and utilizes a cumulative physiological score based on EPOC and TRIMP scores. Training load may be calculated according to U.S. Pat. No. 7,192,401 (B2) "Method for monitoring accumulated body fatigue for determining recovery during exercise or activity", incorporated herein.

The step 104 of the training status calculation shown in FIG. 1B utilizes weekly training load calculations provided by the calculation module 32. Relative weekly training load may be determined based on user's activity class where activity class may be based on user's VO2max and monthly training load (28 day cumulative training load), user's age and gender. Relative training load may be represented by, for example, 6 levels (0-5). Relative training load is 0 if absolute weekly training load is 0. If absolute training load is more than 0 relative training load is determined according to FIG. 4.

Figure 4:
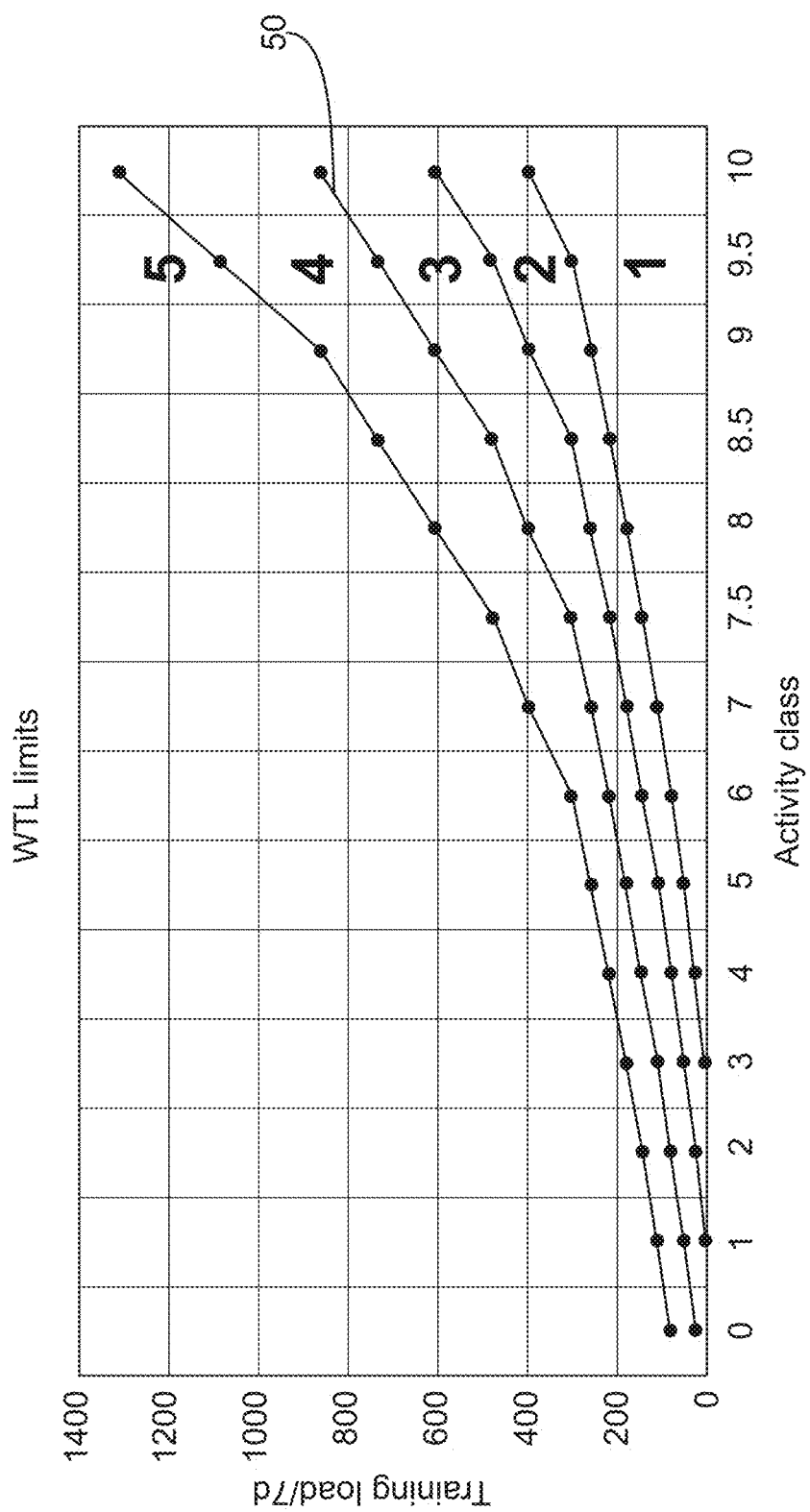
FIG. 4 represents relative weekly training load lower limits (0-5)

Referring now to FIG. 4, activity class is a general descriptor of a person's fitness or training history, placed on a 0-10 scale, wherein 0 represents a person who is essentially entirely sedentary, and 10 is a highly trained individual who exercises regularly. Each plot line of FIG. 4 represents the lower limit of the cumulative training load. By way of example, plot line 50 represents the line wherein a person that exceeds a particular training load will be given a relatively weekly training load value of 4. An athlete with an activity class of "8" that exceeds an absolute training load over a 7-day period of 400 may therefore be given a relative training load value of 4. However, a different person with an activity class of "9" with a similar absolute training load may only receive a relative training load value of 3.

Relative weekly training load is used as part of step 104 in the training load calculation. Referring again to FIG. 1B, depending on the determination of the value of relative weekly training load, different training status 105 may be determined, or the system may take an additional step of accounting for the weekly training load trend. As a person skilled in art understands, relative weekly training load is a value that tells whether the person is training "enough" with respect to his/her activity class. Values of 0 to 1 can be considered as "too easy" training load whereas 2 corresponds to "light/easy training" 3 to "moderate training", 4 to "strenuous training" and 5 to "very hard training", for example. Therefore, when relative training load is between 3 and 4, and user is therefore at his/her target load range, training can be considered "unproductive" if VO2max correspondingly decreases.

Step 105 uses a training load trend to determine whether absolute weekly training load is decreasing relative to the previous month's training load according to predetermined criteria. The training load trend calculation is performed as follows:

$$\text{Training load trend} = \text{Weekly training load peak sum} / \text{Monthly training load peak sum}$$

where the weekly training load peak sum is the sum of all of the training load peaks from the previous 7 days, and monthly training load peak sum is a similar sum, calculated over 28 days. As shown in FIG. 1B, step 104, the criteria for influencing training status is whether the training load in decreasing. Alternatively, the system may consider whether the training load is increasing or staying relatively the same, which may be particularly relevant if additional training statuses are implemented.

In an alternative embodiment, exceptions are included relating to the training status determination of FIGS. 1A-1B. The training status of status "4—Recovery" and status "5—Peaking" may not be outputted when certain criteria is met:

a) the relative weekly training load value has been 0-2 throughout the previous 7-day period OR b) if there is at least one day during last 7-day period when the weekly training load value has been 1 AND VO2max trend has been decreasing.

The exceptions exist in situations when the training load is decreasing but the previous weeks have already been so low that the current training load is zero or close to it. In these situations, the system will instead output a training status of "0—Detraining".

Figure 3:
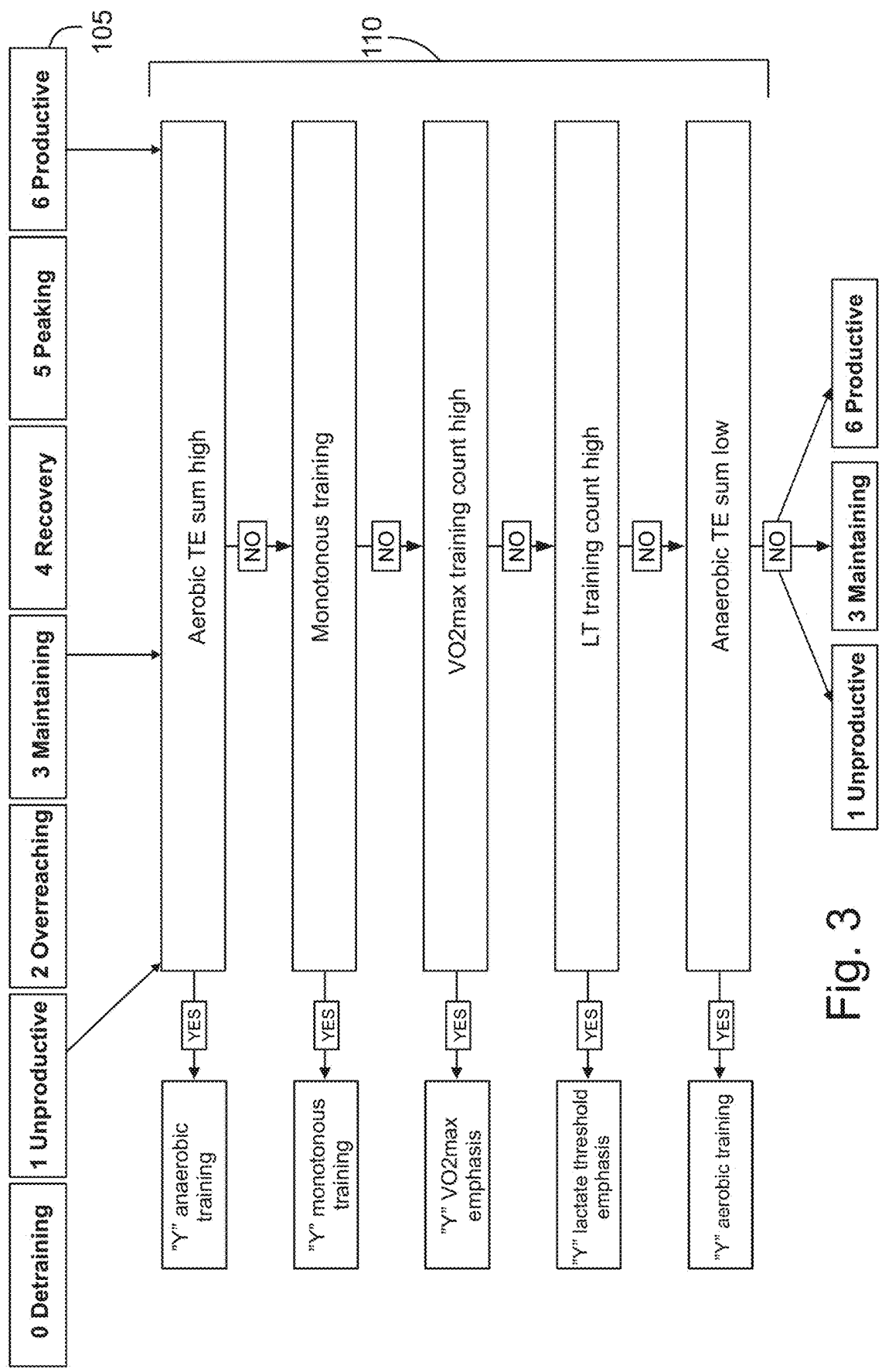
FIG. 3 represents calculation of advanced feedback in addition to basic feedback

Referring now to FIG. 3, advanced feedback on training status may be given after calculation of training status 105. The advanced feedback is based on derivative variables from the data obtained as described above and shown in FIG. 1B.

Various examples of the advanced additional feedback 110 are also shown, and may include identifying the proportion of aerobic training or anaerobic training, the relative variety in the intensity or duration of the training, or the amount of training related to specific physiological thresholds that occur during exercise. A variety of other calculations may also be performed using well-known calculations using the supplied data that are not explicitly described in the present invention. The advanced feedback may make several conclusions. The feedback is not limited to singular pieces of feedback, and the training may be determined to fall into multiple categories if suitable.

The advanced additional feedback provides an additional level of specificity that is not described in the training statuses. Additional information relating to training status are related to the variations in type of training. These may include, but are not limited to, such variables as aerobic versus anaerobic training, the relative variety in the intensity or duration of the training, or the different types of threshold training. Other well-known identifiable trends from the supplied data that are not explicitly described in this patent may also be used to further enhance the level of feedback provided.

Table 1 illustrates a calculation flow. A female user has monitored her exercises during one month. There has been used following terms. The term "peak" is calculated EPOC-peak during an exercise. "Type" refers to the type of exercise (0=run, 1=cycling, empty=not known).

The host process with ETE-software determines the characteristics of each exercise (VO2max, peak, age, sex, exercise type) after they are performed, and stores it in a resident memory. Thus, the left side (VO2max, Peak, Age, Sex, Type) of table grows row by row and is continuously available.

TABLE 1

| date | VO2max | Peak | Age | Sex | Type | VO2max trend | WTL | WTL Trend | STATUS |
|---|---|---|---|---|---|---|---|---|---|
| 9 Jun. 2017 | 52.1 | 48.0 | 29 | 1 | 1 | 0 | 1 | 2 | NO_RESULT |
| . . . | | | | | | | | | |
| 14 Jun. 2017 | 51.5 | 94.1 | 29 | 1 | 1 | 2 | 3 | 2 | NO_RESULT |
| 14 Jun. 2017 | | 80.9 | 29 | 1 | 0 | 2 | 3 | 2 | NO_RESULT |
| 15 Jun. 2017 | | 93.5 | 29 | 1 | 0 | 2 | 3 | 2 | MAINTAINING |
| 16 Jun. 2017 | | 111.0 | 29 | 1 | 0 | 2 | 3 | 2 | MAINTAINING |
| 17 Jun. 2017 | | 127.9 | 29 | 1 | 0 | 2 | 3 | 2 | MAINTAINING |
| 18 Jun. 2017 | | 104.4 | 29 | 1 | 0 | 2 | 3 | 2 | MAINTAINING |
| 18 Jun. 2017 | | 30.5 | 29 | 1 | 0 | 2 | 3 | 2 | MAINTAINING |
| 19 Jun. 2017 | | 108.1 | 29 | 1 | 0 | 2 | 3 | 2 | MAINTAINING |
| 19 Jun. 2017 | 51.2 | 83.4 | 29 | 1 | 1 | 2 | 4 | 3 | PRODUCTIVE |
| 20 Jun. 2017 | 50.9 | 90.3 | 29 | 1 | 1 | 2 | 4 | 3 | PRODUCTIVE |
| . . . | | | | | | | | | |
| 26 Jun. 2017 | | 88.1 | 29 | 1 | 0 | 1 | 2 | 1 | UNPRODUCTIVE |
| 27 Jun. 2017 | 51.0 | 69.9 | 29 | 1 | 1 | 2 | 2 | 1 | RECOVERY |
| 28 Jun. 2017 | 51.3 | 77.2 | 29 | 1 | 1 | 3 | 2 | 2 | PRODUCTIVE |

TABLE 1-continued

| date | VO2max | Peak | Age | Sex | Type | VO2max trend | WTL | WTL Trend | STATUS |
|---|---|---|---|---|---|---|---|---|---|
| 29 Jun. 2017 | | 106.8 | 29 | 1 | 0 | 3 | 3 | 2 | PRODUCTIVE |
| 30 Jun. 2017 | | 121.8 | 29 | 1 | 0 | 3 | 3 | 2 | PRODUCTIVE |
| 30 Jun. 2017 | 51.6 | 66.9 | 29 | 1 | 1 | 3 | 3 | 3 | PRODUCTIVE |
| 1 Jul. 2017 | | 0.0 | 29 | 1 | | 3 | 3 | 2 | PRODUCTIVE |
| 2 Jul. 2017 | | 100.4 | 29 | 1 | 0 | 3 | 3 | 2 | PRODUCTIVE |
| 3 Jul. 2017 | 52.2 | 67.0 | 29 | 1 | 1 | 3 | 3 | 2 | PRODUCTIVE |
| 4 Jul. 2017 | | 98.2 | 29 | 1 | 0 | 3 | 3 | 2 | PRODUCTIVE |
| 4 Jul. 2017 | 51.9 | 100.0 | 29 | 1 | 1 | 3 | 3 | 2 | PRODUCTIVE |
| 5 Jul. 2017 | 51.7 | 82.9 | 29 | 1 | 1 | 2 | 3 | 2 | MAINTAINING |
| 6 Jul. 2017 | | 80.8 | 29 | 1 | 0 | 2 | 3 | 2 | MAINTAINING |
| ... | | | | | | | | | |
| 10 Jul. 2017 | 50.8 | 54.6 | 29 | 1 | 1 | 1 | 3 | 2 | UNPRODUCTIVE |

The right side (in the table) on the other hand is temporal data having the selection parameters VO2max_trend, Weekly Training_Load (WTL) and WTL_trend which are calculated only when desired. Number coding for VO2max trend-values: 0=not known/not available, 1=decreasing, 2=unchanged and 3=increasing). Number coding for WTL trend-values: 0=decreasing, 1=stable, 2=Increasing. The software from THA-library is first called and loaded. The training status "STATUS" is returned to the host process, which presents it in a display. After the result has been outputted to the host process, the child process and its temporal data in one row vanish.

The advanced feedback is provided as supplementation to the original training status calculation and if none of the advanced feedback criteria is confirmed the system will output the training status as normal.

In alternative embodiment, the system may take into account training type when calculating training status. If data contains VO2max values from both running and cycling a specific rule can be applied to get VO2max trend as accurate as possible. In these cases, training status may be calculated based on VO2max values from an exercise type that contains more VO2max estimates in a 14-day window. VO2max from cycling may only be compared to cycling VO2max and VO2max from running may only be compared to running VO2max values since mixing VO2max estimates from different exercise types might skew results. VO2max data source (running/cycling) may not be allowed to change more than once a week, keeping the same activity source for at least 7 days. If there are equal amount of running VO2max and cycling VO2max estimates training status can be calculated using VO2max values of the exercise type whichever was used last.

In the cases when there are more than one VO2max estimates inside a single day the highest value may be selected to determine the VO2max trend calculation.

In one exemplary embodiment, in the case where no new exercise data has been input, the system will still be able to provide select training status data. The training statuses of "0—Detraining", "4—Recovery", and "no status" statuses can be outputted without new exercise data. Other states require at least a new training session to update the training status.

In an alternative embodiment, other physiological signals other than heart rate may be used to measure training load. For example, electromyography (EMG) signals could be used to measure muscular training load. End users may be able to utilize the various apparel that is available on the market that measures EMG-signals to measure muscular training load data and can provide data for the system.

In an alternative embodiment, the host system 30 may also consider additional factors in the calculation of fitness level as well as training load. These factors may include environmental information, such as altitude, humidity, temperature, or wind. For example, VO2max estimates measured in high altitude and/or high temperature/humidity may be converted to correspond normalized conditions using some predetermined criteria. Other factors may include considerations related to sub-types of sports, like the difference in the speed of bicycling surface between road and mountain biking, the amount of climb or descent, the technicality of the course in cycling or running or the differences between exercising outdoors and indoors/on a stationary exercise machine. The present system is not limited in its ability to consider any factor that may affect fitness level or training load.

In alternative embodiment, the system may also consider the rate of change in both training load and measured VO2 max from week to week. For example, if the training load is detected as increasing at an unusually high rate, the system may provide additional information related to the risk of injury from excessive increase in training load. An unusually large decrease in training load may also bring up other relevant feedback. Similar types of feedback may be given with reference to rate of change of the VO2 max estimate, as it may indicate illness or overtraining, for example.

In still another alternative embodiment, with respect to FIGS. 1A, 1B and 2, heart rate variability based recovery state, sleep quality and/or stress levels measured during daily life or other separate measurements may be taken into account in training status determination. Calculation of such metrics may take place in host system 30 and calculation of said metric is disclosed e.g. in US issued U.S. Pat. No. 7,330,752 (B2) "Procedure for Detection of Stress by Segmentation and Analyzing a Heart Beat Signal", US issued U.S. Pat. No. 9,519,755 (B2) Method and System for Evaluating a Physiological State Depicting a Person's Resources" and/or US patent application 2016324462 (A1) "Method and System for Providing Feedback Automatically on Physiological Measurements to a User". For example, if training load is high, results from a night time measurement or separate recovery tests could be used as additional information in training status determination. For example, if the VO2max trend is maintaining, the relative weekly training load value is 4-5 and recovery status is poor then training status could be determined as Overreaching instead of Productive. Of course, in one possible embodiment of the described invention VO2max trend could be replaced with recovery state information. For example, 1) decreasing, 2) maintaining and 3) increasing VO2max trends could be replaced with 1) poor recovery, 2) moderate recovery and 3) good recovery states, respectively. This kind of embodiment would be suitable for example in team-sports like ice-hockey or basketball, where athletes typically train indoors and train with exercises where it may be difficult to get estimates of their VO2max, but estimation of recovery state instead is very possible.

Training status is presented to a user in a variety of different ways, exemplary embodiments are shows in FIGS. 5-8. The presentations of training status may be adapted as appropriate to the device's display that is being used. FIG. 5 shows a number of text alternatives for describing training status, including a longer description of each status, a text representation of the relatively weekly training load value and VO2Max trend, a sample explanation of the training that may lead to selection of that particular training status, and a sample piece of text that may be presented to a user providing guidance about future training. Training status could be updated daily or weekly. If training status is updated on a weekly basis (instead of daily basis) one possible method for analyzing weekly status is to show the mode of the daily status during the week. If two or more different statuses appear as frequently during last 7 days then weekly status is chosen according to pre-set priority rules, which may include a specific activity chosen by the user, and averaging of the most common activity over a specific period of time.

Figure 6:
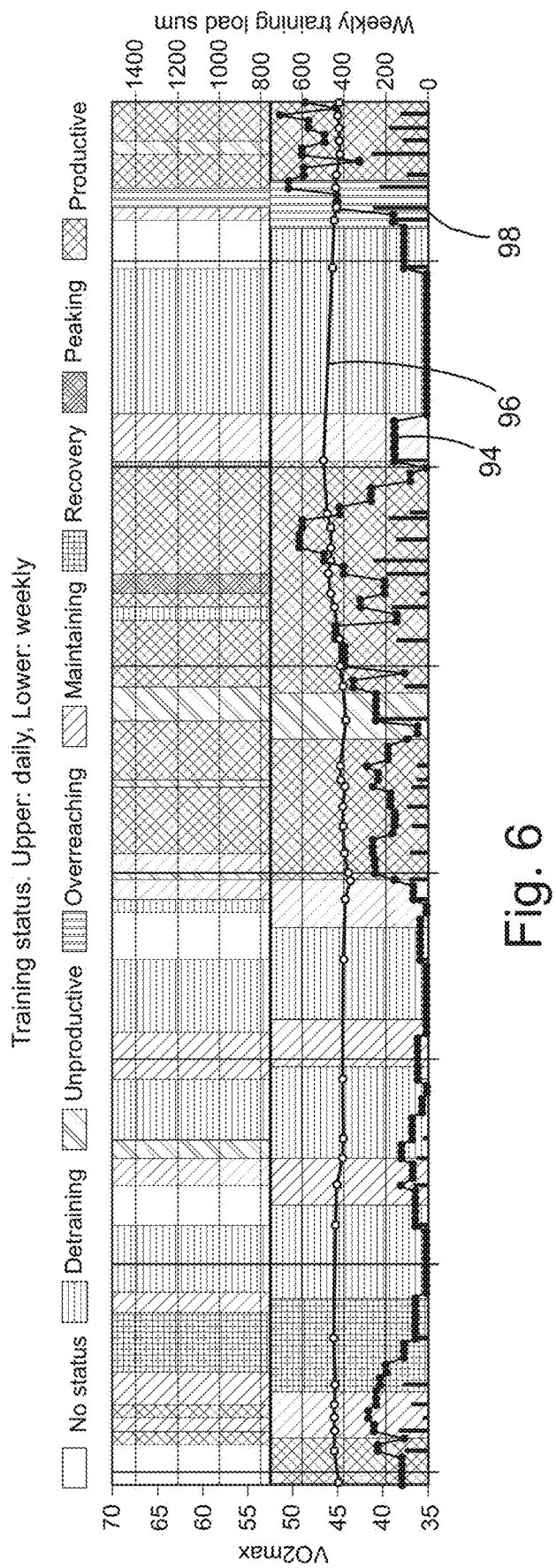
FIG. 6 represents a training status example during a 7-month training period, particularly weekly training status

FIG. 6 shows an example month-by-month training status chart, showing a total of 7 months of past training, with both a daily level portion and a weekly level portion. The various training statuses are illustrated by shading. The embodiment described above where the mode of the daily status is selected as a weekly status is illustrated in FIG. 6, wherein the most frequently daily training status of the week makes up the resultant weekly training status measurement. VO2Max line 94 represents the fluctuation of the user's fitness level over time, while training load sum line 96 represents the cumulative absolute training load of the previous 7 days. Optionally, training load peak 98 may additionally be displayed.

Figure 7:
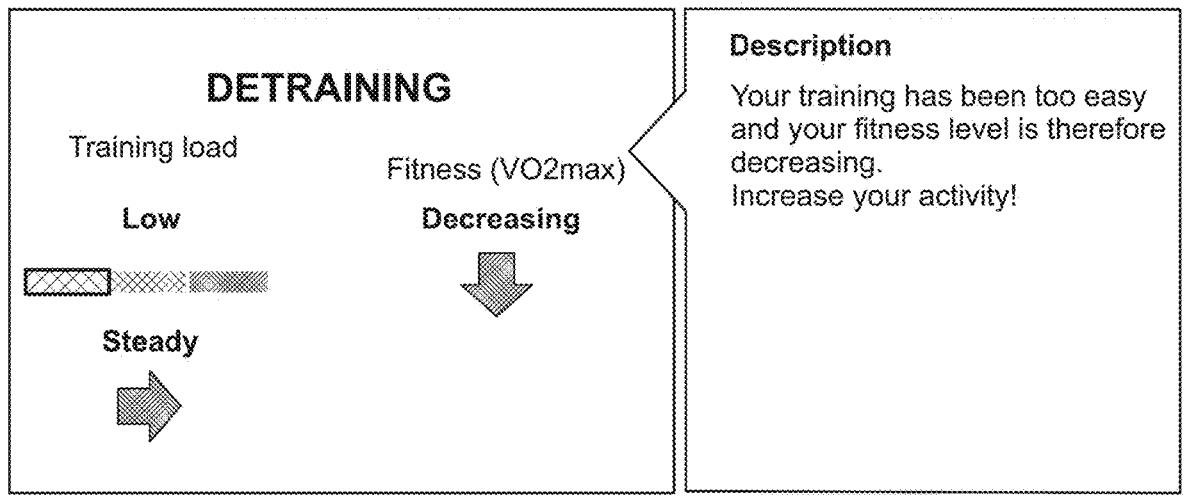
FIG. 7 represents an example to show training status to the user

FIG. 7 is an illustrative example of how training status may be shown to a user, which may be displayed on an ordinary wrist top device having a host system for physiological measurements and analysis. The amount of information may vary based on the physical space available on the display, and may, for example, be displayed on multiple pages, or using graphical representations. In this example, "training load" is illustrated by an absolute training load graphic as well as a training load trend graphic. Fitness level is represented by VO2Max and also shows a trend graphic. All of this information is derived from calculation module 32 in FIG. 1, and examples of possible text descriptions were shown in FIG. 5.

Figure 8:
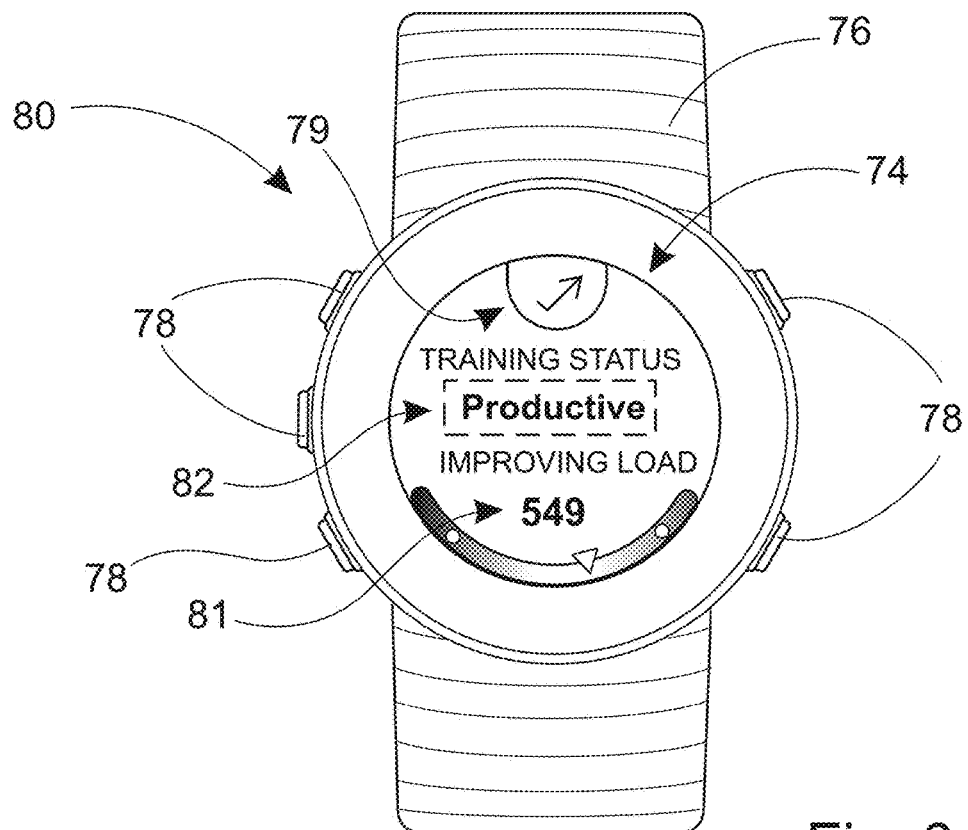
FIG. 8 represents another example to show training status to the user

A further illustrative example of the presentation of the training status is shown in FIG. 8 showing a wrist top device 80 (worn on the wrist of a user held on the wrist by a strap 76) forming a user interface and used by a conventional fitness enthusiast or sportsperson. It has a display 74 with several fields. The result, the actual training status is shown literally in the field 82 and graphically in the field 79. Absolute weekly training load is shown in the field 81. The training status display may optionally have further screens that may be scrolled through to see further elaboration of the training status information, such as the information illustrated in FIG. 7.

Training Status Using an HRV-Value Instead of VO2max Information

Figure 10:
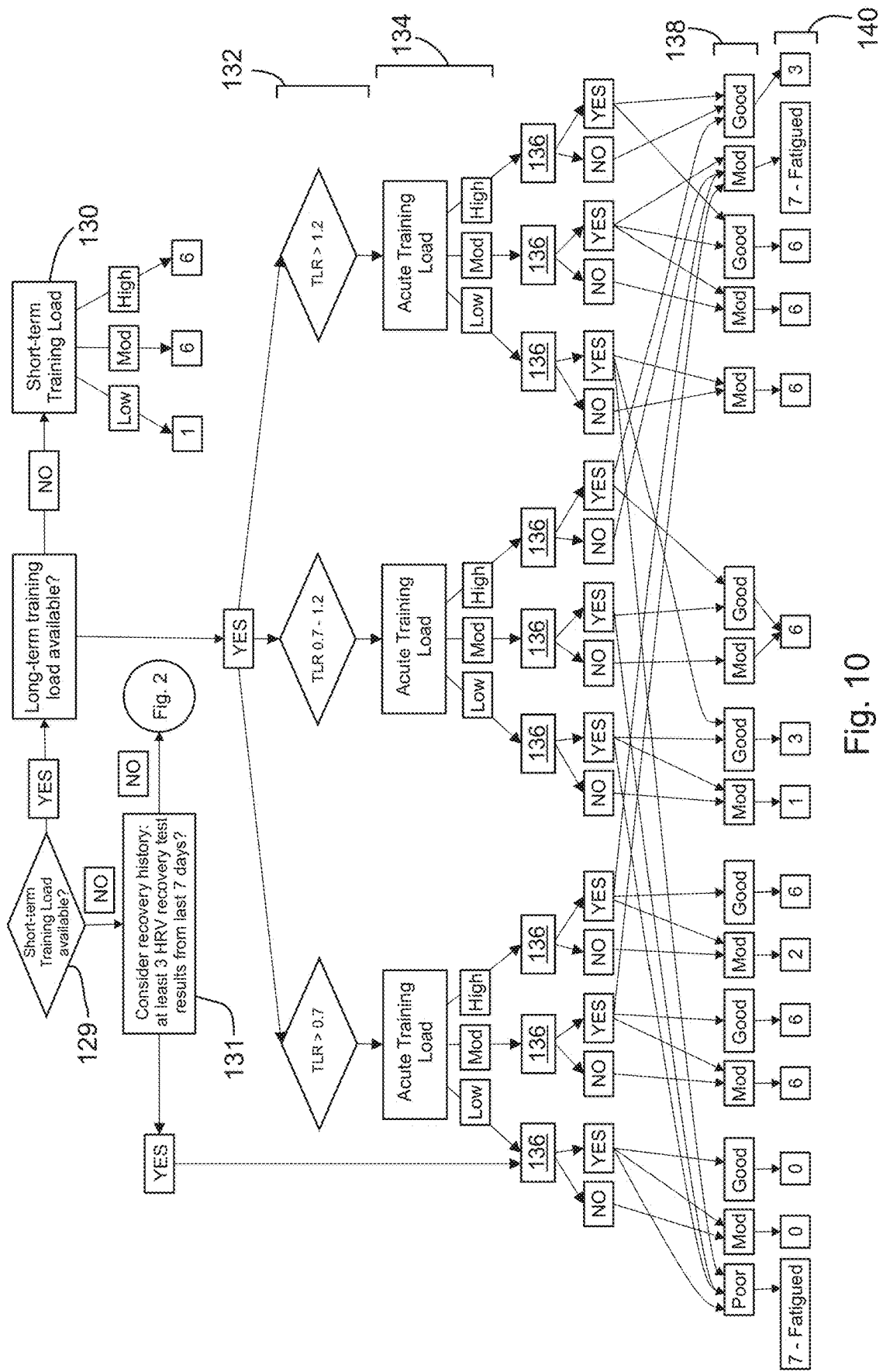
FIG. 10 represents alternative embodiment for calculation of training status The following Table 1 may show exemplary definitions and abbreviations of terms used in the exemplary embodiments described herein.

In another alternative embodiment, shown in FIG. 10, a heart rate variability recovery test may be used to determine a training status. A recovery test describes how well an athlete is recovered from previous training sessions, and may produce a numerical score or a text result representing the athlete is within a particular zone, such as "poor recovery", "moderate recovery" (mod) or "good recovery". The relationship between training load and recovery levels can also provide sufficient detail to make a training status assessment. Similar to the flow chart of FIG. 1B, the training status also considers whether the training load is increasing or decreasing from week-to-week, wherein a particular training load that is decreasing while having a low recovery score may result in a different training status as when the training load is increasing. In addition, calculation of the weekly training load may use a calculation of the ratio between short-term and long-term training load, such as comparing the weekly training load to the previous month's training load, respectively. In this alternative embodiment, the parameter "readiness" is determined through HRV monitoring.

Referring still to FIG. 10, the short-term to long-term training load ratio (TLR) of step 132, compares recent training load to the training load over a longer period of time, which may determine whether the intensity of the most recent bouts of training are increasing relative to previous time periods. The ratios of step 132 serve as example upper and lower limits and said limits may be adjusted as appropriate to reflect the demands of a particular sport. In step 134, the short-term training load, which may be the training of the last 7 days, is determined. The training load measurement may take the form of "low", "moderate", and "high" as shown in FIG. 10, or may for example be in a similar form to the embodiment shown in FIG. 1B, which uses the numbered weekly training load calculation described in FIG. 4.

In step 136 of FIG. 10, the system will determine whether at least 3 HRV recovery tests have been performed in the previous 7 days. A normal expectation is that at least 3 recovery tests done in a week to provides the most accurate measurement of a person's recovery over the previous week of training, though the system will still provide a training status assessment even without a specific minimum of HRV recovery tests. As shown in step 138, the different levels of recovery test scores will result in different training statuses in step 140, which may use the similar number and descriptive word as described in step 105 of FIG. 1B. For clarity, only the numerical training status designations are shown in FIG. 10, and correspond to those disclosed earlier. In this alternative embodiment, it is possible that additional training statuses are utilized that accurately describe a person's status. For example, when having low training load but are still having poor recovery scores, may be described using an appropriate word, such as "fatigued". Unavailability of any of the input described above, short- or long-term workload may also still produce a training status, as shown in step 129 where there is no short-term workload available, step 130 when there is no long-term workload, or step 131 where there is insufficient HRV recovery tests.

Training Status without VO2max Information

As shown in FIG. 1, if the system does not detect at least 7 days of training history, a fitness level value and a fitness level trend, the system will not be able to run a complete training status assessment. However, the system is capable of making a limited training status calculation utilizing some partial information that may be available.

Referring to FIG. 2, an exemplary method of the calculation of limited training status when insufficient training history and VO2Max information is available is shown. In this example, in step 108, if the relative training load value is between 1-3 and absolute training load is decreasing, the system will output a training status value of "recovery". Similarly, in step 109 if there is enough data from previous workouts to still be able to calculate a weekly training load value that is greater than 0, relative training load values of 1 or 5 will also provide a training status values of "detraining" or "overreaching", respectively. The remaining relative training load values from 2 to 4 will not provide one of the training status values, though the system will continue and attempt to determine other feedback alternatives.

Additional Information

The limited statuses may be identical to those performed in the additional feedback 110 described above and in FIG. 3. These training statuses may include additional descriptions on the level of training load change, the distribution of the training type, such as between aerobic anaerobic or hard and easy training or information on the variety of intensity of duration of the training. General, non-specific descriptions of the training is also provided in step 112, shown as light training, moderate training, and strenuous training. These non-specific determinations are based on the remaining relative weekly training load values of 2-4, respectively.

Example Implementation:

The system and method according to the exemplary embodiments can be applied in many kinds of devices as would be understood by a person of ordinary skill in the art. For example, a wrist top device with a heart-rate transmitter, a mobile device such as a phone, tablet or the like, or other system having CPU, memory and software therein may be used.

Figure 9:
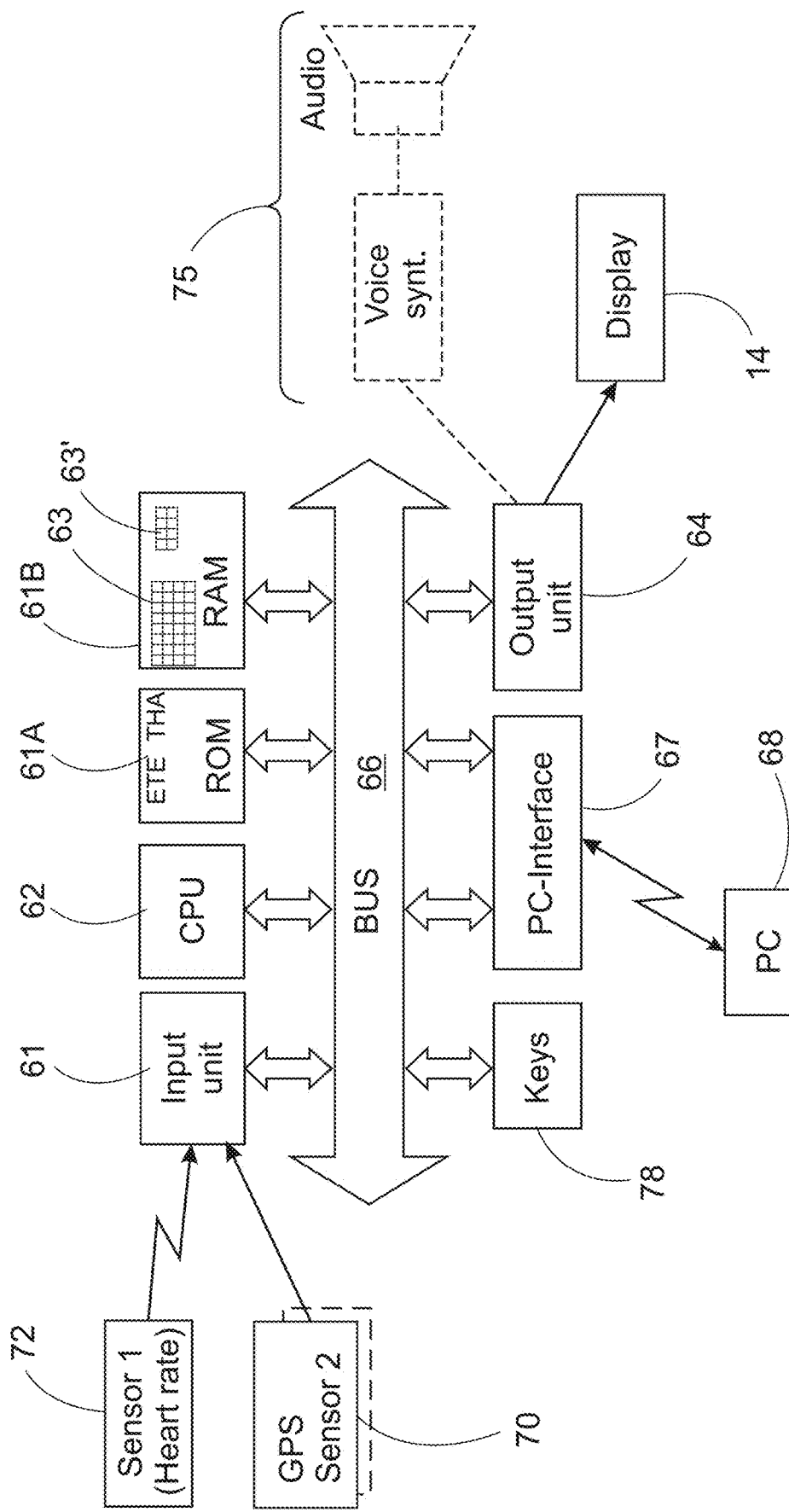
FIG. 9 represents an example of a hardware assembly

According to exemplary FIG. 9, the implementation may include an assembly built around a central processing unit (CPU) 62. A bus 66 may transmit data between the central unit 62 and the other units. The input unit 61, ROM memory 61A RAM memory 61B including a dedicated memory 63' for the training status application and memory 63 for the host system, keys 78, PC connection 67, and output unit 64 may be connected to the bus.

The system may include a data logger which can be connected to cloud service, or other storage as would be understood by a person of ordinary skill in the art. The data logger may measure, for example, physiological response and/or external workload.

A heart rate sensor 72 and any sensor 70 registering external workload may be connected to the input unit 61, which may handle the sensor's data traffic to the bus 66. In some exemplary embodiments, the PC may be connected to a PC connection 67. The output device, for example a display 75 or the like, may be connected to output unit 64. In some embodiments, voice feedback may be created with the aid of, for example, a voice synthesizer and a loudspeaker 75, instead of, or in addition to the feedback on the display. The sensor 70 which may measure external workload may include any number of sensors, which may be used together to define the external work done by the user.

More specifically the apparatus presented in FIG. 9 may have the following parts for determining a training status:

a heart rate sensor 72 configured to measure the heartbeat of the person, the heart rate signal being representative of the heartbeat of the user;

optionally at least one sensor 70 to measure an external workload during an exercise, and a data processing unit 62 operably coupled to the said sensors 72, 70, a memory 61A, 61B operably coupled to the data processing unit 62, the memory may be configured to save background information of a user, for example, background data including an earlier performance level, user characteristics, and the like.

The apparatus may include dedicated software configured to execute the embodiments described in the present disclosure.

The training status application requires RAM—memory 100-400 bytes (×8 bits), preferably 120-180 bytes. Each day requires 4 byte. Explained by way of example, 150 bytes covers 38 days, wherein the highest VO2max [16 bits], its exercise type [2 bits] and the sum of training load peaks [14] are recorded. Generally, calculation has a window of plurality of days, e.g. 15-60 days, preferably 30-50 days.

The invention claimed is:

1. A method for determining a training status of a user from plurality of exercises using a device with a heart rate sensor, a processor, memory, and software, the determined training status being selected from a fixed group of alternatives depicting a unique physical condition of the user,
   wherein heart rate data is recorded during each exercise using the heart rate sensor, and chosen exercise characteristics of each executed exercise are determined using recorded heart rate data, and after each exercise the determined characteristics of each executed exercise are stored in the memory, the chosen exercise characteristics including values of at least the following variables:
   a date of the exercise,
   a value depicting physical readiness level in terms of a VO2max-value for exercise during the exercise; and
   a value depicting a training load of the exercise,
   wherein when the plurality of exercises have been executed, values of selection variables are calculated using the stored exercise characteristics in the memory, and
   the training status is determined using sequential predetermined selection rules, each rule being connected to one unique variable of said selection variables, wherein each selection rule uses a calculated value of its selection variable to limit a number of remaining alternatives and, after all selection rules have been sequentially used, only one alternative is selected.

2. A method according to claim 1, wherein there are three selection rules with three selection variables, namely a fitness level (VO2max) trend, a weekly training load (WTL) and a WTL trend.

3. The method according to claim 1, wherein the variable of the training load is a peak value regarding a training effect measured as a disturbance level of homeostasis.

4. The method according to claim 1, wherein the number of training status alternatives is at least 5, these alternatives comprising at least Detraining, Maintaining, Recovery, Overreaching and Productive.

5. The method according to claim 1, wherein an output device is implemented in at least one of the following: a heart rate monitor, a fitness device, a mobile phone, a PDA device, a wrist top computer, a tablet computer or a personal computer.

6. The method according to claim 1, further comprising a selection of additional information according to at least one additional variable depicting at least one of: anaerobic training effect, training variability or high intensity training count.

7. The method according to claim 1, wherein a type of exercise is stored as part of the characteristics of each exercise.

8. The method according to claim 7, wherein at least one selection variable is calculated using data of a same exercise type.

9. The method according claim 1, wherein values of selected variables of each day are recorded and summed in a sliding window of a plurality of past days, the selected variables including at least a highest VO2max, its type of exercise, a sum of peaks of training loads, and the VO2max trend being calculated from the values of the highest VO2max of a same type.

10. An apparatus for determining a training status of a user from a plurality of exercises using a device with a heart rate sensor, the device having a processor, memory, resident memory and software, the determined training status being an alternative of a fixed group of alternatives each of them depicting a unique physical condition of the user,
   said software being arranged to monitor each exercise using the heart rate sensor and to determine chosen exercise characteristics of each executed exercise and store them in a resident memory, the chosen exercise characteristics including values of at least:
   a date of the exercise,
   a value depicting readiness level in terms of a VO2max-value for exercise during the exercise; and
   a value depicting a training load of the exercise
   said software is adapted to validate the training status calculation, when the plurality of exercises has been executed and calculate values of selection variables using the stored exercise characteristics in the resident memory, and
   when called, determine the training status using sequential pre-determined selection rules, each rule being connected to one unique variable of said selection variables, where each selection rule using a calculated value of its selection variable is limiting the number of remaining alternatives and to select one alternative representing the training status after all selection rules have been sequentially used.

11. The apparatus according to claim 10, wherein the apparatus is at least one of: a heart rate monitor, a fitness device, a mobile phone, a PDA device, a wrist top computer, a tablet computer or a personal computer.

12. The apparatus according to claim 10, wherein a dynamic memory in a RAM memory is allocated 100-400 bytes (×8 bits) for calculation of training status in a child process.

13. The apparatus according to claim 10, wherein the software includes a basic library (ETE) for monitoring the exercises and determining characteristics of the plurality of exercises in a host process using a memory dynamic and storing the exercise characteristics in a resident memory, and an auxiliary library software (THA) to determine the training status as a child process using characteristics in the resident memory.

* * * * *